United States Patent [19]

Alvarez et al.

[11] Patent Number: 5,792,218
[45] Date of Patent: Aug. 11, 1998

[54] N-ALKYL AMMONIUM ACETONITRILE ACTIVATORS IN DENSE GAS CLEANING AND METHOD

[75] Inventors: Vincent E. Alvarez, Livermore, Calif.; James W. Arbogast, Scottsdale, Ariz.; James E. Deline, Livermore, Calif.; Lafayette D. Foland, Dublin, Calif.; Thomas W. Kaaret, Alamo, Calif.; Kevin A. Klotter, Livermore, Calif.; Michael J. Petrin, Antioch, Calif.; William L. Smith; Alfred G. Zielske, both of Pleasanton, Calif.; James D. Mitchell, Alamo, Calif.

[73] Assignee: The Clorox Company, Oakland, Calif.

[21] Appl. No.: 758,541

[22] Filed: Nov. 29, 1996

Related U.S. Application Data

[63] Continuation-in-part of Ser. No. 475,292, Jun. 7, 1995, Pat. No. 5,739,327.

[51] Int. Cl.⁶ .............................. D06L 3/02; C01B 15/00; C11D 3/39
[52] U.S. Cl. .............................. 8/111; 8/137; 252/186.39; 510/312
[58] Field of Search .................. 252/186.39, 186.38; 8/111, 137; 510/312; 544/86, 163, 402; 546/246

[56] References Cited

U.S. PATENT DOCUMENTS

| | | | |
|---|---|---|---|
| 2,425,693 | 8/1947 | Cook et al. | 558/459 |
| 2,489,950 | 11/1949 | Blicke | 558/205 |
| 2,625,547 | 1/1953 | Lawson et al. | 544/171 |
| 2,774,758 | 12/1956 | Yanko | 544/163 |
| 2,848,450 | 8/1958 | Rudner et al. | 544/164 |
| 2,851,458 | 9/1958 | Billinghurst | 544/163 |
| 2,868,786 | 1/1959 | Siemer et al. | 544/171 |
| 3,532,735 | 10/1970 | Morgan | 558/455 |
| 3,689,470 | 9/1972 | Shachat et al. | 526/312 |
| 3,772,275 | 11/1973 | Hernestam et al. | 536/7.4 |
| 3,780,092 | 12/1973 | Samour et al. | 560/222 |
| 3,873,583 | 3/1975 | Walz et al. | 554/103 |

(List continued on next page.)

FOREIGN PATENT DOCUMENTS

| | | |
|---|---|---|
| 20303520 | 8/1988 | European Pat. Off. . |
| 883075582 | 8/1988 | European Pat. Off. . |
| 912011707 | 5/1991 | European Pat. Off. . |
| 912012606 | 5/1991 | European Pat. Off. . |
| 0790244 | 2/1997 | European Pat. Off. . |
| 25035829 | 1/1975 | Germany . |
| 25557691 | 12/1975 | Germany . |
| 26204455 | 5/1976 | Germany . |
| 62-225871 | 9/1987 | Japan . |
| 63-167157 | 7/1988 | Japan . |
| 1230773 | 9/1989 | Japan . |
| 6136391 | 10/1992 | Japan . |

OTHER PUBLICATIONS

Hart et al., "Some New Quaternary–Substituted Alkyl Morpholinium Chlorides and Pyrrolidinium Alkyl Sulfates," *Journal of Organic Chemistry*, 22:1 (Mar. 5, 1957), pp. 86–88.

*Primary Examiner*—Joseph D. Anthony
*Attorney, Agent, or Firm*—Majestic, Parsons, Siebert & Hsue

[57] ABSTRACT

Nitrile activators, such as N-alkyl ammonium acetonitrile activators, are combined with a source of active oxygen as cleaning and bleaching compositions. Preferred activator embodiments of the invention include salts of N-methyl morpholinium acetonitrile, N-butyl morpholinium acetonitrile, N-hexyl morpholinium acetonitrile, and N-octyl morpholinium acetonitrile. A particularly preferred activator embodiment is an N-methyl morpholinium acetonitrile salt. The nitrile and active oxygen react to form a bleaching agent which is applied to a stain on an article. The treated stain is contacted with dense gas so as to provide substantially non-aqueous stain removal. One embodiment is a composition in which the nitrile and active oxygen are disposed in the dense carbon dioxide.

21 Claims, 1 Drawing Sheet

U.S. PATENT DOCUMENTS

| | | | |
|---|---|---|---|
| 3,882,035 | 5/1975 | Loffelman et al. | 510/313 |
| 4,086,175 | 4/1978 | Kravetz et al. | 510/314 |
| 4,134,889 | 1/1979 | Distler et al. | 546/230 |
| 4,164,511 | 8/1979 | Distler et al. | 558/346 |
| 4,199,466 | 4/1980 | Benson, Jr. | 510/314 |
| 4,215,003 | 7/1980 | Finley et al. | 8/111 |
| 4,328,226 | 5/1982 | Witek et al. | 514/239.5 |
| 4,342,872 | 8/1982 | Grier et al. | 546/186 |
| 4,397,757 | 8/1983 | Bright et al. | 252/186.41 |
| 4,551,526 | 11/1985 | Mai et al. | 544/163 |
| 4,737,498 | 4/1988 | Banasiak et al. | 514/237.8 |
| 4,751,015 | 6/1988 | Humphreys et al. | 510/376 |
| 4,904,406 | 2/1990 | Darwent et al. | 510/376 |
| 4,915,863 | 4/1990 | Aoyagi et al. | 510/376 |
| 4,921,631 | 5/1990 | Gradwell et al. | 252/186.38 |
| 4,978,770 | 12/1990 | Aoyagi et al. | 558/455 |
| 5,093,022 | 3/1992 | Sotoya et al. | 510/376 |
| 5,106,528 | 4/1992 | Francis et al. | 252/186.23 |
| 5,236,616 | 8/1993 | Oakes et al. | 252/186.38 |
| 5,281,361 | 1/1994 | Adams et al. | 252/186.38 |
| 5,330,677 | 7/1994 | Sotoya et al. | 252/186.38 |
| 5,370,742 | 12/1994 | Mitchell et al. | 134/10 |
| 5,399,746 | 3/1995 | Steiger et al. | 560/251 |
| 5,405,412 | 4/1995 | Willey et al. | 8/111 |
| 5,431,843 | 7/1995 | Mitchell et al. | 252/186.38 |
| 5,460,747 | 10/1995 | Gosselink et al. | 510/220 |
| 5,591,378 | 1/1997 | Deline et al. | 252/186.38 |

FIG. 1.

N-ALKYL AMMONIUM ACETONITRILE ACTIVATORS IN DENSE GAS CLEANING AND METHOD

This application is a CIP of Ser. No. 08/475,292 filed Jun. 7, 1995 now U.S. Pat. No. 5,739,327.

FIELD OF THE INVENTION

The present invention generally relates to N-alkyl ammonium acetonitrile compounds, and more particularly for use of these compounds as activators for hydrogen peroxide in cleaning and bleaching compositions including dense gas.

BACKGROUND OF THE INVENTION

Peroxy compounds are effective bleaching agents, and compositions including mono- or diperoxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid can present a problem of storage stability for compositions consisting of or including peroxyacids.

One approach to the problem of reduced bleaching activity of peroxyacid compositions has been to include activators of peroxyacids. U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester.

U.S. Pat. No. 4,778,618, Fong et al., issued Oct. 18, 1988 provides novel bleaching compositions comprising peracid precursors with the general structure wherein R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $N^+R_3^\alpha$, wherein $R^\alpha$ is $C_{1-30}$ alkyl; and where L is a leaving group which can be displaced in a peroxygen bleaching solution by peroxide anion. U.S. Pat. Nos. 5,182,045, issued Jan. 26, 1993, and 5,391,812, issued Feb. 21, 1995, inventors Rowland et al. are similar, but are polyglycolates of the Fong et al. monoglycolate precursors, or activators.

U.S. Pat. No. 4,915,863, issued Apr. 10, 1990, inventors Aoyagi et al., discloses compounds said to be peracid precursors that have nitrile moieties. U.S. Pat. No. 5,236,616, issued Aug. 17, 1993, inventors Oakes et al., discloses compounds said to be cationic peroxyacid precursors that have nitrile moieties. These nitrile containing activators do not contain a leaving group, such as the Fong et al. leaving groups, but instead include a quaternary ammonium group suggested as activating the nitrile and said, upon reaction with hydrogen peroxide, to generate a peroxy imidic acid as bleaching species. The Aoyagi et al. activators include an aromatic ring, which tends to cause fabric yellowing.

Thus, new peroxygen activators that do not gray or harm fabrics and that provide superior bleaching remain desirable for bleaching and cleaning applications. Additionally, environmentally safe alternatives to presently used dry cleaning materials (e.g. perchloroethylene) in non-aqueous, or dry cleaning processes, would be desirable.

U.S. Pat. No. 5,431,843, issued Jul. 11, 1995, inventors Mitchell et al. describes cleaning compositions in which a dense gas is combined with a perhydrolysis system containing an organic activator and a source of hydrogen peroxide. Suggested activators are carbon carbonyl compounds such as esters, nitriles, imides, oximes, carboxylic acids, acid anhydrides, and the like, which in the presence of a source of hydrogen peroxide react to form a corresponding organic peracid. Exemplified are nonanoyloxyglycoylbenzene and nonanoyloxyglycoylphenyl sulfonate as activators.

SUMMARY OF THE INVENTION

It is an object of the present invention to provide nitrile activators, such as N-alkyl ammonium acetonitrile activators, with a source of active oxygen in a dense gas as cleaning and bleaching compositions.

In one aspect of the present invention, novel nitrile activators are provided that have the Formula IA, Formula IB, or Formula IC structure:

FORMULA IA

FORMULA IB

FORMULA IC

In the general Formula I structure (with A, B, and C subparts), A is a saturated ring formed by a plurality of atoms in addition to the $N_1$ atom. The ring atoms include at least one carbon atom and at least one of O, S and N atoms. $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. "Y" is at least one counterion.

The Formula IA and IC structures have a $R_1$ substituent bonded to the $N_1$ atom. The $R_1$ substituent includes either:

(a) a $C_{1-24}$ alkyl or alkoxylated alkyl where the alkoxy is $C_{2-4}$; a $C_{4-24}$ cycloalkyl; a $C_{7-24}$ alkaryl; or a repeating or nonrepeating alkoxy or alkoxylated alcohol, where the alkoxy unit is $C_{2-4}$;

or (b) —$CR_2R_3C\equiv N$ where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$.

The Formula IB dimer structure has $R_2'$ and $R_3'$ chosen from the same moieties as $R_2$ and $R_3$ and which may be the same as $R_2$ and $R_3$ or be different, and has a $R_4$ linking group bonded to the $N_1$ atom. The $R_4$ substituent includes a polyoxyalkylene group with 1 to 24 oxyalkylene units or an alkylene group with 1 to 24 carbons, as well as thioethers.

The Formula IC compounds have $R_5$, which includes a methylene or a repeating methylene —$(CH_2)_n$— and n is 1 to about 20.

The Formula I compounds have a quaternary nitrogen atom ($N_1$) so at least one appropriate counterion (Y) will be associated therewith.

The novel compounds with the Formula I structure are particularly useful when formulated as cleaning compositions that include a source of active oxygen and are in a dense gas.

Preferred activator embodiments of the invention include salts of N-methyl morpholinium acetonitrile, N-butyl morpholinium acetonitrile, N-hexyl morpholinium acetonitrile, and N-octyl morpholinium acetonitrile, which are illustrated by Formula II (with "n" being 0 to 23 and where "Y" is the at least one counterion).

FORMULA II

A particularly preferred activator embodiment of the invention is an N-methyl morpholinium acetonitrile salt (sometimes designated "MMA" where "n" of Formula II is zero).

Compositions of the invention are useful for cleaning and bleaching. Where the dense gas is the preferred carbon dioxide, then the compositions can be used for non-aqueous cleaning of stained fabrics (e.g. "dry cleaning").

In another aspect of the invention, a novel bleaching agent is provided that is a reaction product derived from reaction between the Formula I structure nitriles and a dense gas in which this reaction product is disposed. For performing substantially non-aqueous stain removal in accordance with the invention, the bleaching agent is applied to the stain on an article and the article is contacted with dense gas during or after the application of the bleaching agent. The article is then separated from the dense gas. The bleaching agent may be derived by reaction of the Formula I nitrile and active oxygen at the site of the stain or may be derived by admixing these reactants before application to the stain.

DETAILED DESCRIPTION OF The PREFERRED EMBODIMENTS

Compositions of the invention include certain nitriles as activators having the structure illustrated by Formula I (A, B, and C). The $N_1$ atom of the Formula I (including the A, B, and C subparts) compound is part of a saturated ring, illustrated by "A" in Formula I.

FORMULA IA

FORMULA IB

FORMULA IC

This saturated ring of which $N_1$ is a part has a plurality of atoms. The saturated ring illustrated by ring "A" in Formula I has at least one hetero atom in the saturated ring in addition to the $N_1$, preferably wherein the ring includes an oxygen atom, a sulfur atom, or one or two additional nitrogen atoms.

The at least one nitrogen in the saturated ring ($N_1$) shown in Formula I is N-acetonitrile substituted and also quaternized. Without being bound by theory, we believe that the electron withdrawing nature of the quaternary nitrogen may be increased by being part of a saturated, heterocyclic ring and may also function to improve the hydrophilic character of the oxidant.

A substituent $R_1$ will be bonded to the $N_1$ atom of the Formula IA structure and additionally a nitrile moiety (—$CR_2R_3C\equiv N$) is bonded to the $N_1$ atom, where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. The $R_1$ substituent may be a $C_{1-24}$ alkyl or alkoxylated alkyl where the alkoxy is $C_{2-4}$, a $C_{4-24}$ cycloalkyl, a $C_{7-24}$ alkaryl, a repeating or nonrepeating alkoxy or alkoxylated alcohol, where the alkoxy unit is $C_{2-4}$, and illustrative such groups are, for example, where j=1 to 24. The $R_1$ substituent may also be another —$CR_2"R_3"C\equiv N$ (represented by $CR_2"R_3"C\equiv N$), and wherein $R_2"$ and $R_3"$ are each H, a $C_{1-24}$ alkyl, cycloalkyl, or alkaryl, or a repeating or nonrepeating alkoxyl or alkoxylated alcohol where the alkoxy unit is $C_{2-4}$, and illustrative such groups are:

where j=1 to 24.

Formulas IB and IC illustrate dimeric embodiments of the invention where $R_4$ and $R_5$ each is a linking group. This linking group $R_4$ may be a polyoxyalkylene group with 1 to 24 oxyalkylene units, such as groups derived from ethylene oxide, propylene oxide, butylene oxide, or mixtures thereof. Examples are:

where k=1 to 24. Thioethers may also be used. The $R_4$ linking group may also be an alkylene group with 1 to 24 carbons. $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. $R_2'$ and $R_3'$ chosen from the same moieties as $R_2$ and $R_3$ and which may be the same as $R_2$ and $R_3$ or be different.

The Formula IC compounds have $R_5$, which includes a methylene or a repeating methylene —$(CH_2)_n$— and n is 1 to about 20.

Particularly preferred, saturated rings forming the cyclic configuration A of Formula I contain six atoms including the $N_1$ atom, but the number of atoms forming the cyclic configuration can range from 3 to 9. When two heteroatoms are present with the cyclic configuration A of Formula I, then a three member ring is unusual; but, for the cyclic configuration B of Formula III shown below, where there may only be $N_1$ as the sole heteroatom, then three membered rings are very likely.

Particularly preferred activator embodiments are illustrated by Formula II (where "Y" is at least one counterion and "n" is 0 to 23.

FORMULA II

Counterions

Since compounds of the invention are typically quaternized, they will include at least one counterion (designated as "Y"), which can be substantially any organic or inorganic anion, such as, but not limited to, chloride, bromide, nitrate, alkyl sulfate, and the like. Dimeric activators (e.g. Formula IB) will include at least two counterions, or a doubly charged anion, such as sulfate, carbonate, and the like.

Bleaching and Cleaning Compositions

Compounds having the Formula I structure have a saturated ring formed by a plurality of atoms, broadly ranging from 3 to 9, although preferably containing 6 atoms including the $N_1$ atom. Preparation of these compounds will most conveniently start with a compound already having the formed ring. For example, a number of preparations of inventive nitriles hereinafter described will begin with morpholine (see, e.g., the Formula II structure). An example of three membered rings is aziridine, e.g., N-methylacetonitrile aziridinium; as an example of four membered rings there is azetidine, e.g., N-ethylacetonitrile azetidinium; as an example of five membered rings there is pyrrolidine, e.g., N-butylacetonitrile pyrrolidinium; as an example of six membered rings, in addition to morpholine, there is piperidine, e.g., N-methylacetonitrile piperidinium; as an example of seven membered rings there is homopiperidine, e.g., N-ethylacetonitrile homopiperidinium; as an example of eight membered rings there is tropane, e.g., N-methylacetonitrile-8azabicyclo [3.2.1] octane; and, as an example of nine membered rings there is octahydroindole, e.g., N-methylacetonitrile octahydroindolinium.

The peroxide or active oxygen source for compositions of the invention may be selected from the alkaline earth metal salts of percarbonate, perborate, persilicate and hydrogen peroxide adducts and hydrogen peroxide. Most preferred are sodium percarbonate, sodium perborate mono- and tetrahydrate, and hydrogen peroxide. Other peroxygen sources may be possible, such as monopersulfates and monoperphosphates. For example, a commercially available source of active oxygen is available from DuPont under the trademark OXONE for a monopersulfate oxidizing compound.

The range of peroxide to activator is preferably determined as a molar ratio of peroxide to activator. Thus, the range of peroxide to each activator is a molar ratio of from about 0.1:1 to 100:1, more preferably about 1:1 to 10:1 and most preferably about 2:1 to 8:1. This peracid activator/peroxide composition should provide about 0.5 to 100 ppm A.O., more preferably about 1 to 50 ppm peracid A.O. (active oxygen), and most preferably about 1 to 20 ppm peracid A.O., in a dense gas matrix.

In addition to the necessary nitrile activator and source of active oxygen, optional additional additives and adjuvants may be included in compositions of the invention. For example, pH adjusting agents can be included such as sources of alkalinity, which will be further discussed hereinafter. Other adjuvants may include surfactants.

Surfactants with which the activators and active oxygen compositions may be combined or admixed include linear ethoxylated alcohols, such as those sold by Shell Chemical company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 1–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides, phosphine oxides, sulfoxides and their ethoxylated derivatives.

Delivery System

The nitrile activator and source of active oxygen are reactive with each other when in an appropriate form and preferably are delivered with or without optional additives and adjuvants in a dense gas vehicle.

The term "dense gas" applies to gases which are subjected to greater than usual (atmospheric) pressure or lower than usual temperature (room temperature, 21.1° C.) to enhance density.

A preferred gas for densification is carbon dioxide. Carbon dioxide ($CO_2$) is a colorless gas which can be recovered from coal gassification, synthetic ammonia and hydrogen generation, fermentation and other industrial processes.

In the invention, densified carbon dioxide is preferably used as a cleaning agent for removing soils and stains from fabrics, in conjunction with the nitrile activator and active oxygen source. Densified carbon dioxide is carbon dioxide which has been placed under greater than atmospheric pressure or low temperature to enhance its density. In contrast to carbon dioxide used in pressurized canisters to deliver foamed products, e.g., fire extinguishers or shaving creams, densified carbon dioxide is preferably at much greater pressures, e.g., 800 p.s.i. and greater. It has been found that density, rather than temperature or pressure alone, has much greater significance for enhancing the solvent-like properties of carbon dioxide.

Other types of dense gases which would be of utility herein include densified carbon dioxide and supercritical carbon dioxide. The concept of dense carbon dioxide encompasses these other types of carbon dioxides. Other supercritical fluids appear suitable for use as dense gases, and include liquids capable of gassification, e.g., ammonia, lower alkanes ($C_{1-5}$) and the like.

The amount, or volume, of densified carbon dioxide or other supercritical fluid would depend on the type of substrate, temperature and pressure involved, as well as the volume of the container for such densified gas. Generally, an amount which is effective to remove the stain is used. Thus, for the purposes of this invention, cleaning-effective amounts are used.

The dense gas vehicle, preferably dense carbon dioxide, can play several functions in the inventive compositions. A primary function is to lift off and carry away the moieties that had caused the stain or soil being treated. A second function will typically be as a carrier or matrix for bringing the nitrile and active oxygen into contact with each other and with the stain and the soil to be treated. For performing the first described function, the inventive composition can be viewed as a combination of dense gas and the reaction product of nitrile and active oxygen, while for performing the second function the composition can be viewed as a combination of the nitrile, a source of active oxygen, and the dense gas. Thus, the particular inventive formulations will be adapted for their intended uses, such as will be in various combinations of solid or liquid forms and in view of the timing desired for mixing the two reactive components.

For example, the nitrile activator component and the active oxygen source component could both be used directly in a solid form, although this is not a preferred way of practicing the invention. They would both preferably employed in as pure a form as possible, if storage stable, or in the form of a stabilized powder, granule or prill, for example, for improved storage stability until use. Suitable means for predissolving the nitrile activator and the active oxygen source could be employed, such as by exposing them to a suitable cosolvent. An illustrative manner for predissolving solid components would be to place the required amounts in an unpressurized chamber (premixing chamber), which can be sealed, pressurized with the densified gas or cosolvent of choice. This chamber is connected to the main cleaning chamber to allow mixing of all cleaning components simultaneously. Alternatively, the contents of the pressurized premixing chamber could be mixed directly with the densified gas of choice prior to introduction into the main cleaning chamber to ensure a completely homogenous mixture. The premixing chamber could contain a mixing impeller, or a similar mechanical device, to more effectively agitate solids for faster and more complete dissolution prior to combination of the contents with the densified cleaning gas.

Alternatively and preferably, the nitrile activator and the active oxygen source can be employed in liquid form. The materials can be predissolved in a suitable solvent, preferably a solvent that is easily handled in liquid form under normal atmospheric conditions (room temperature and pressure). Preferred solvents for predissolved activator solutions include hydrocarbons, such as n-hexane, n-heptane, benzene, toluene, p-xylene, alcohols, such as methanol, ethanol, and isopropanol, and water, as examples. Preferred solvents for predissolved peroxide source solutions include alcohols, such as methanol, ethanol, and isopropanol, and water, as examples. Dispensing of the liquid components can be achieved in a means similar to the solutions of the solid components described above by means of a premixing chamber charged with a suitable cosolvent or densified gas of choice. Alternatively, the liquid components could be injected directly into the cleaning chamber by use of appropriate metering pumps or pistons to deliver a measured and known quantity of both bleach activator and hydrogen peroxide source.

The nitrile activators can be precombined with a hydrogen peroxide source and additional desired components, such as a source of alkalinity, prior to mixing with the densified cleaning gas. Among preferred sources of alkalinity are $NH_3$, monoethanolamine, diethanolamine and triethanolamine. The source of alkalinity could be employed in a solid form, preferably in as active a form as possible (such as anhydrous sodium carbonate or sodium hydroxide in preference to hydrated salts such as sodium carbonate monohydrate) so as to minimize the content of water introduced to the system. The source of alkalinity could also be a gas, such as ammonia ($NH_3$) or a liquid, such as monoethanolamine or an aqueous solution of a suitable alkalinity source.

A preferred embodiment of the invention is the combination of dense carbon dioxide, MMA with a methyl sulfate counterion and hydrogen peroxide in a 300 ml high pressure chamber such that 50 mg of the activator is allowed to react with 67 mg of 10% hydrogen peroxide in an atmosphere of dense carbon dioxide. Such a combination could come about by, but is not limited to, the placement of the activator onto a stain or soiled fabric and the injection of the peroxide into the carbon dioxide matrix. The resulting reaction forming an activated oxidant performs the bleaching function. However, as will be understood by the above discussion of liquid and solid delivery systems, numerous other methods of delivery of inventive compositions will be possible, including the formation of the activator in situ from precursor materials.

Figure 1:
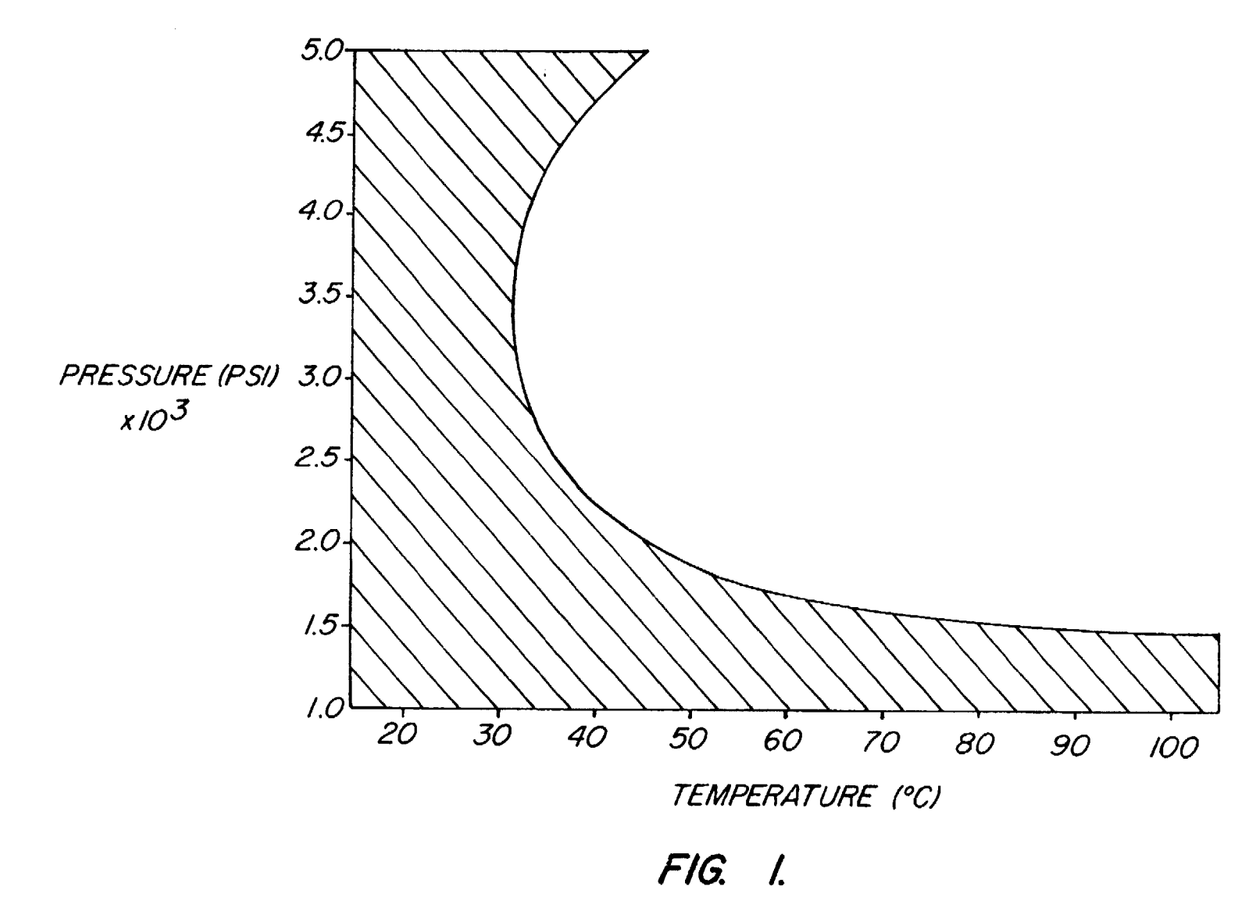
FIG. 1 graphically illustrates temperature and pressure conditions within a hatched area in which compositions of the invention are preferably held.

With reference to FIG. 1 and use of carbon dioxide as the dense gas, a temperature range from slightly below about 20° C. to slightly above about 100° C. is indicated on the horizontal axis and a pressure range of from about 1000 psi to about 5000 psi on the vertical axis illustrates broadly the temperature and pressure ranges in which embodiments of the invention are preferably practiced. As is seen by the hatched region of FIG. 1, preferred conditions are between about 900 psi to 2000 psi at temperatures between about 20° C. to about 45° C., with more preferred conditions being pressure from about 900 psi to about 1500 psi at temperatures between about 20° C. and 100° C. or from about 3500 psi to about 5000 psi at temperatures between about 20° C. and 37° C. Where fabrics are being cleaned, one preferably works within a temperature range between about 20° C. to about 100° C. In addition, it has been found within this range that processes which raise the temperature prior to decompression reduce the damage to polymeric parts.

Suitable compounds as the dense gas are either liquid or are in a supercritical state within the temperature and pressure hatched area illustrated by FIG. 1. The particularly preferred dense gas in practicing this invention is carbon dioxide due to its ready availability and environmental safety. The critical temperature of carbon dioxide is 31° C. and the dense (or compressed) gas phase above the critical temperature and near (or above) the critical pressure is often referred to as a "supercritical fluid." Other densified gases known for their supercritical properties as well as carbon dioxide, may also be employed by themselves or in mixture. These gases include methane, ethane, propane, ammonium-butane, n-pentane, n-hexane, cyclohexane, n-heptane, ethylene, propylene, methanol, ethanol, isopropanol, benzene, toluene, p-xylene, chlorotrifluoromethane, trichlorofluoromethane, perfluoropropane, chlorodifluoromethane, sulfur hexafluoride, and nitrous oxide.

Practice of the invention may include the cleaning method described by U.S. Pat. No. 5,370,742, issued Dec. 6, 1994, inventors Mitchell et al., incorporated herein by reference. More broadly, however, the invention can be practiced for cleaning as described by U.S. Pat. No. 5,431,843, already referenced.

Examples 1, 2, and 3 illustrate preparations of preferred nitrile activators for the invention.

EXAMPLE 1

In general, N-quaternary acetonitrile compounds are readily prepared from N-acetonitrile precursors by employing selected alkyl halides and using well-known synthetic approaches, such as are described by Menschutkin, Z. Physik. Chem., 5, 589 (1890), and Z. Physik. Chem., 6, 41 (1890); Abraham, Progr. Phys. Org. Chem., 11, 1 (1974); and Arnett, J. Am. Chem. Soc., 102, 5892 (1980).

Specifically detailed preparations of four preferred activator embodiments are described below as illustrative.

EXAMPLE 1A
Preparation of N-Methyl Morpholinium Acetonitrile (MMA):

To a solution of 30 g of morpholine acetonitrile in 75 ml of ethyl acetate was added 22.5 ml of dimethyl sulfate, corresponding to approximately equivalent molar amounts of the two reagents. The resulting solution was mechanically stirred in an oil bath maintained at 40° C. After 10 minutes of stirring, a semi-solid precipitate having a brownish coloration formed and settled on the bottom of the flask. HPLC (high pressure liquid chromatography) analysis showed at least 4 undesirable side products, which were removed. The remaining solution was again heated to 40° C. and reacted for an additional 16 hours. After this time, the resulting white paste was filtered and washed with ethyl acetate. MMA was isolated after drying this filtrate as a free flowing off-white solid in 79% yield, having a melting point of 99°–101° C. The purity of the MMA was determined by HPLC to be greater than 95%.

EXAMPLE 1B
Preparation of N-Hexyl Morpholinium Acetonitrile (HMA):

Combined were 44.08 g of hexylbromide, 29.88 g morpholine, and 28.0 g anhydrous sodium carbonate with 150 ml of acetone in a large round bottom flask. This mixture was refluxed for 8 hours at the boiling point of acetone or approximately 60° C., then cooled to room temperature and the solid sodium carbonate filtered. Acetone was removed using a roto-evaporator. The resulting oil was dissolved in ether and washed twice with water and once with brine solution. The ether solution was dried over anhydrous sodium sulfate. After filtering, ether was removed in-vacuo leaving 45.2 g of a lightly-colored oil in 98.8% yield. Gas chromatography showed the oil to be N-hexyl morpholine in approximately 95% purity. Combined were 2.0 g of N-hexylmorpholine with 0.95 g of chloroacetonitrile in a small vial. After capping the vial was heated to 55° C. for approximately 24 hours. A viscous oil resulted which solidified upon addition of a small amount of ethylacetate. The solid was filtered and washed with excess ethylacetate, then dried in a vacuum dessicator resulting in 2.3 g of final white solid, in a yield of approximately 84%. Carbon-13 NMR analysis revealed the desired product present with no other detectable impurities noted.

EXAMPLE 1C
Preparation of N-Octyl Morpholinium Acetonitrile (OMA):

Combined were 51.5 g of octylbromide, 29.88 g morpholine, and 28.0 g anhydrous sodium carbonate with 150 ml of acetone in a large round bottom flask. This mixture was refluxed for 8 hours at the boiling point of acetone or approximately 60° C., then cooled to room temperature and the solid sodium carbonate filtered. Acetone was removed using a roto-evaporator. The resulting oil was dissolved in ether and washed twice with water and once with brine solution. The ether solution was dried over anhydrous sodium sulfate. After filtering, ether was removed in-vacuo, leaving a slightly-colored oil. Gas chromatography showed the oil to be N-octyl morpholine, obtained with a yield of 98% and having greater than 95% purity. Combined were 2.3 g of N-octyl morpholine together with 1.0 g of chloroacetonitrile in a small vial. After capping the vial was heated to 55° C. for approximately 24 hours. A viscous oil resulted which solidified upon addition of a small amount of ethylacetate. The solid was filtered and washed with excess ethylacetate, then dried in a vacuum dessicator resulting in the isolation of a white solid, in a yield of approximately 84%. Carbon-13 NMR analysis revealed the desired product present with no other detectable impurities noted.

EXAMPLE 1D
Preparation of N-Butyl Morpholinium Acetonitrile (BMA):

Combined were 10 g of butylbromide, 6.36 g morpholine, and 28.0 g anhydrous sodium carbonate with 150 ml of acetone in a large round bottom flask. This mixture was refluxed for 8 hours at the boiling point of acetone or approximately 60° C., then cooled to room temperature and the solid sodium carbonate filtered. Acetone was removed using a roto-evaporator. The resulting oil was dissolved in ether and washed twice with water and once with brine solution. The ether solution was dried over anhydrous sodium sulfate. After filtering, ether was removed in-vacuo leaving 5.15 g of product estimated at 49.3% yield. Gas chromatography showed the product to be N-butyl morpholine in approximately 95% purity. Combined 7.2 g of N-butyl morpholine together with 3.0 ml of chloroacetonitrile in a small vial. After capping the vial was heated to 60° C. for approximately 24 hours. An oil resulted which solidified upon addition of a small amount of ethylacetate. The solid was filtered and washed with excess ethylacetate, then dried in a vacuum dessicator resulting in a white solid in nearly stoichiometric yield. Carbon-13 NMR analysis revealed the desired product present with no other detectable impurities noted.

EXAMPLE 2

Dimer embodiments of the invention, for example such as illustrated by Formula IB, may be prepared as follows.

EXAMPLE 2A
1,6-Bis(4-cyanomethylmorpholinium)hexane Dichloride (HDMMA):

100 ml of morpholine (1.147 mole) and 150 ml ethylacetate (EtOAc) were added to 500 ml Morton flask equipped with reflux condenser, thermometer, mechanical stirrer, and heating mantel. 25 ml of 1,6-dichlorohexane (0.172 mole) was added slowly to flask at room temperature. This was refluxed for 48 hours. Gas chromatogram showed 90% completion of the reaction. The product 1,6-bismorpholinohexane was purified from reaction mixture by vacuum filtration to remove the morpholine hydrochloride, and the light yellow filtrate was purified by adsorption chromatography. $^{13}$C NMR showed a spectrum consistent with structure with very minor impurities. Gas chromatography showed an approximate purity of 98.2% based upon peak areas. The collected amount of 1,6-bismorpholinehexane was 30.0 g, which corresponds to a yield of 66.6%.

12.68 g of bismorpholinohexane (0.049 mole) and 55 ml EtOAc were added to 500 ml Morton flask equipped with reflux condenser, pressure equalizing dropping funnel, mechanical stirrer, and heating mantel. 15 ml of chloroacetonitrile (0.238 mole) was added slowly to flask at room temperature. This was refluxed for 5 hours. Light brown solid precipitated from the solution, and the solid was isolated by vacuum filtration, rinsed with EtOAc, and dried overnight in vacuum oven at ambient temperature. $^{13}$C NMR showed a spectrum consistent with structure with a significant, but small impurity of starting amine. Collected 12.6 g of product, corresponding to 57.1% yield from this step.

EXAMPLE 2B
1,2-Bis(2-(4-cyanomethylmorpholinium)ethoxy)ethane Dichloride (EODMMA):

100 ml of morpholine (1.147 mole) and 150 ml EtOAc were added to 500 ml Morton flask equipped with reflux condenser, thermometer, mechanical stirrer, and heating mantel. 25 ml of 1,2-bis(2-chloroethoxy)ethane (0.160 mole) added slowly to flask at room temperature. This was refluxed for 16 hours. Product 1,2-bis (2-morpholinoethoxy) ethane was purified from reaction mixture by vacuum filtration to remove the morpholine hydrochloride, and the light yellow filtrate was purified by adsorption chromatography. 18.4 g of product was collected, and a gas chromatogram showed an approximate purity of 98.2% based upon peak areas. The collected amount of 1,2-bis(2-morpholinoethoxy)ethane corresponds to a yield of 39.2%.

14.94 g of 1,2-bis(2-morpholinoethoxy)ethane (0.051 mole) and approximately 100 ml EtOAc were added to 500 ml Morton flask equipped with reflux condenser, pressure equalizing dropping funnel, mechanical stirrer, and heating mantel. 25 ml of chloroacetonitrile (0.397 mole) was added slowly to flask at room temperature. This was refluxed for 8 hours. Light brown solid precipitated from the solution, and the solid was very tacky and stiff. The mechanical stirrer froze solid in the material. Mother liquor was decanted off the solid, and the solid was redissolved in methanol. The solvent was evaporated in a recrystallization dish for several days. Mother liquor reacted further for an additional 8 hours without any stirring, with more product forming. The product from the second heating was collected in a manner identical to first. 14.6 g of product was collected from the first reaction period and 5.5 g from the second reaction period. Together the two reactions yielded 20.1 g of product, corresponding to 85.4% yield. $^{13}$C NMR shows spectrum consistent with the proposed structure with a small impurity of methanol.

EXAMPLE 3A
Preparation of 2,6-bis(4-methylmorpholinium) pimelonitrile (BMMP)

Step 1. Dissolve 45.15 g of the sodium bisulfite addition product of glutaraldehyde in 130 mL of water in a large Morton flask fitted with mechanical stirrer. Separately, dissolve 19.46 g potassium cyanide in 45 mL of water. To the glutaraldehyde-bisulfite solution, add 112.3 g of a 25% aqueous solution of morpholine, with stirring. Cool reaction in ice-bath and add potassium cyanide solution dropwise, but at fast rate. Entire reaction is under positive nitrogen pressure, with outlet gases bubbled through a 5.25% sodium hypochlorite solution. Let temperature of reaction slowly come to room temperature and let stir overnight. In the morning, filter white solid and wash well with water. Treat filtrate and water washings with sodium hypochlorite to destroy any remaining cyanide. Dry product in vacuum over to give 39.3 g of a white solid (92% yield). Recrystallize from water/ethanol to give 31.5 g (74% yield) product as white crystals. Carbon-13 NMR shows no impurities.

Step II. To 15.0 g of the product from the preceding reaction, was added 40 g of dimethylsulfate in a 100 mL round bottom flask. The mixture was mechanically stirred and heated to 60° C. for one hour. Cooled reaction mixture and diluted with ethanol. Filtered resulting solid to give 16.9 g (61% yield) of pure product (by NMR).

EXAMPLE 3B
Preparation of N-(1-cyanobutyl-N-methyl morpholinium methyl sulfate To a 1 L Morton flask was added 70.0 g of sodium bisulfite and 110 mL of water. The flask was fitted with a mechanical stirrer and stirred to dissolve the bisulfite. Next, 49.1 g of butyaldehyde was added dropwise via an addition funnel. The now warm reaction mixture was cooled in an ice-bath while a separate solution of 44.3 g of potassium cyanide dissolved in 70 mL of water was prepared. To the now cool butyaldehydebisulfitesolution was added 237.2 g of 25% aqueous morpholine dropwise at a fast rate. Immediately after the morpholine addition was complete, the potassium cyanide solution was added dropwise with an addition funnel. During the cyanide addition, the entire flask was maintained under a positive nitrogen atmosphere, with the exit gases bubbled through a 5.25% solution of sodium hypochlorite. The reaction mixture was slowly equilibrated to room temperature, and then stirred overnight. In the morning, the oil which had formed was decanted off, and the remaining aqueous phase was extracted with diethylether three times. The ether extractions were combined with the oil and dried over anhydrous sodium sulfate. The ether solution was then filtered and the ether removed in vacuo. After pumping on a high-vacuum system for about one hour, the colorless oil had solidified into white, crystalline solid (113.7 g, 100% yield). Carbon-13 NMR showed this white solid to be the desired product in high purity.

The quaternization of N-(1-cyanobutyl)morpholine proceeds in an analogous manner to that already described.

It is to be understood that while the invention has been described above in conjunction with preferred specific embodiments, the description and examples are intended to illustrate and not limit the scope of the invention, which is defined by the scope of the appended claims.

It is claimed:

1. A method of substantially non-aqueous stain removal, comprising:

applying a bleaching agent to the stain on an article, the bleaching agent being derived from reaction between a nitrile and a peroxygen releasing source, the nitrile selected from the group consisting of Formula IA, Formula IB, Formula IC, and mixtures thereof, wherein Formulas IA, IB, and IC have the respective structures (Formula IA)

(Formula IB)

(Formula IC)

wherein A is a saturated ring formed by a plurality of atoms in addition to the $N_1$ atom, the saturated ring atoms to include at least one carbon atom and at least one heteroatom in adition to the $N_1$ atom, the said one heteroatom selected from the group consisting of O, S and N atoms, the substituent $R_1$ bound to the $N_1$ atom of the Formula IA structure is (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, or (e) a —$CR_2"R_3"C\equiv N$, where $R_2, R_3, R_2', R_3', R_2"$, and $R_3"$ are each H, a $C_{1-24}$ alkyl, cycloalkyl, or alkaryl, or a repeating or nonrepeating alkoxyl or alkoxylated alcohol where the alkoxy unit is $C_{2-4}$, the $R_4$ linking group includes a polyoxyalkylene group with 1 to 24 oxyalkylene units, where one or more oxygen atoms may be replaced by a sulfur atom, or an alkylene group with 1 to 24 carbons, and the $R_5$ linking group is a —$(CH_2)_n$— where n is 1 to about 20, and Y is at least one counterion;

contacting the article with dense gas during or after the application of bleaching agent wherein the dense gas is at a pressure of from about 900 psi to about 5000 psi; and separating the article from the dense gas.

2. The method as in claim 1 wherein the bleaching agent is derived by reaction of the reactants at the site of the stain.

3. The method as in claim 1 wherein the bleaching agent is derived by admixture of the reactants before application to the stain.

4. The method as in claim 1 wherein the dense gas includes carbon dioxide.

5. A bleaching agent, comprising:

a reaction product, the reaction product derived from reaction between a nitrile and a peroxygen releasing source, the nitrile selected from the group consisting of Formula IA, Formula IB, Formula IC, and mixtures thereof, wherein Formulas IA, IB, and IC have the respective structures (Formula IA)

(Formula IB)

(Formula IC)

wherein A is a saturated ring formed by a plurality of atoms in addition to the $N_1$ atom, the saturated ring atoms to include at least one carbon atom and at least one heteroatom in addition to the $N_1$ atom, the said one heteroatom selected from the group consisting of O, S and N atoms, the substituent $R_1$ bound to the $N_1$ atom of the Formula IA structure is (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, or (e) a —$CR_2"R_3"C\equiv N$, where $R_2, R_3, R_2', R_3', R_2"$, and $R_3"$ are each H, a $C_{1-24}$ alkyl, cycloalkyl, or alkaryl, or a repeating or nonrepeating alkoxyl or alkoxylated alcohol where the alkoxy unit is $C_{2-4}$, the $R_4$ linking group is a polyoxyalkylene group with 1 to 24 oxyalkylene units, where one or more oxygen atoms may be replaced by a sulfur atom, or an alkylene group with 1 to 24 carbons and the $R_5$ linking group is a —$(CH_2)_n$— where n is 1 to about 20, and Y is at least one counterion; and a dense gas in which the reaction product is disposed, the dense gas being at a pressure of from about 900 psi to about 5000 psi.

6. The bleaching agent as in claim 5 wherein the dense gas is at a pressure of from about 900 psi to about 2000 psi and a temperature between about 20° C. to about 45° C.

7. A cleaning and bleaching composition comprising:

a nitrile having the structure of Formula IA, Formula IB, or Formula IC (Formula IA)

-continued (Formula IB)

(Formula IC)

wherein A is a saturated ring formed by a plurality of atoms in addition to the $N_1$ atom, the saturated ring atoms to include at least one carbon atom and at least one hetero atom in addition to the $N_1$ atom, the said one hetero atom selected from the group consisting of O, S and N atoms, the substituent $R_1$ bound to the $N_1$ atom of the Formula IA structure is (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, or (e) a —$CR_2"R_3"C\equiv N$, where $R_2, R_3, R_2', R_3', R_2''$, and $R_3''$ are each H, a $C_{1-24}$ alkyl, cycloalkyl, or alkaryl, or a repeating or nonrepeating alkoxyl or alkoxylated alcohol where the alkoxy unit is $C_{2-4}$, the $R_4$ linking group is a polyoxyalkylene group with 1 to 24 oxyalkylene units, where one or more oxygen atoms may be replaced by a sulfur atom, or an alkylene group with 1 to 24 carbons, and the $R_5$ linking group is a —$(CH_2)_n$— where n is 1 to about 20, and Y is at least one counterion;

a peroxygen releasing source; and, a dense gas, wherein the dense gas is at a pressure of from about 900 psi to about 5000 psi.

8. The bleaching composition as in claim 7 wherein the peroxygen releasing source is an alkali or alkaline earth metal salt of percarbonate, perborate, persilicate, a hydrogen peroxide adduct, hydrogen peroxide, or a monopersulfate.

9. The composition as in claim 7 wherein the nitrile is a N-methyl morpholinium acetonitrile salt.

10. The composition as in claim 7 wherein the nitrile is a N-ethyl morpholinium acetonitrile salt.

11. The composition as in claim 7 wherein the nitrile is a N-propyl morpholinium acetonitrile salt.

12. The composition as in claim 7 wherein the nitrile is a N-butyl morpholinium acetonitrile salt.

13. The composition as in claim 7 wherein the nitrile is a N-hexyl morpholinium acetonitrile salt.

14. The composition as in claim 7 wherein the nitrile is a N-octyl morpholinium acetonitrile salt.

15. The composition as in claim 7 wherein the nitrile is a N-methyl piperazinium-N,N'-diacetonitrile salt.

16. The composition as in claim 7 wherein the nitrile has Formula IC, $R_1$ is an alkyl with 1 to 20 carbons, $R_2$ is hydrogen, and n is 1 to about 3.

17. The composition as in claim 7 wherein the nitrile is 2,6-bis(4-methylmorpholinium)pimelonitrile, methyl sulfate.

18. The compound as in claim 7 wherein A is a saturated ring formed by four carbon atoms and one oxygen atom in addition to the $N_1$ atom.

19. The compound as in claim 7 wherein A is a saturated ring formed by four carbon atoms and a $N_2$ atom in addition to the $N_1$ atom, with $N_2$ being a secondary amine, a tertiary amine having the substituent —$CR_5R_6CN$, or a quaternary amine having the substituents —$R_5$ and —$CR_5R_6CN$, and wherein $R_5$ and $R_6$ may each be a H or $C_{1-6}$ alkyl.

20. The compound as in claim 7, 18, or 19 wherein the alkylene of the $R_4$ linking group is an alkylene ether or an alkylene thioether.

21. The compound as in claim 20 wherein the linking group is —$(CH_2)_k$, $(CH_2CH_2O)_k$—$(CH_2CH_2)$—, or where k=1 to 24.

* * * * *